United States Patent [19]

Oswald

[11] 3,998,754

[45] Dec. 21, 1976

[54] SURFACE ACTIVE QUATERNARY HIGHER DIALKYL PHOSPHONIUM SALTS

[75] Inventor: Alexis A. Oswald, Mountainside, N.J.

[73] Assignee: Exxon Research & Engineering Co., Linden, N.J.

[22] Filed: July 31, 1974

[21] Appl. No.: 493,253

[52] U.S. Cl. ............................................. 252/351
[51] Int. Cl.$^2$ ....................................... B01F 17/00
[58] Field of Search ............. 260/606.5 F; 252/356, 252/351, 353

[56] References Cited

UNITED STATES PATENTS

| | | | |
|---|---|---|---|
| 1,921,364 | 8/1933 | Lommel et al. ............. | 260/606.5 F |
| 3,230,069 | 1/1966 | Preston ...................... | 260/606.5 F |
| 3,268,323 | 8/1966 | Goyette ...................... | 260/606.5 F |

FOREIGN PATENTS OR APPLICATIONS

| | | |
|---|---|---|
| 589,512 | 12/1959 | Canada |
| 434,810 | 9/1935 | United Kingdom |

OTHER PUBLICATIONS
Chemical Abstracts, vol. 47, 10123c (1953).

*Primary Examiner*—Helen M. S. Sneed
*Attorney, Agent, or Firm*—John P. Corcoran; Joseph J. Allocca

[57] ABSTRACT

Higher dialkyl lower dialkyl phosphonium chloride salts, derived via quaternarization of phosphines with primary chlorides, have unexpected surfactant biocidal properties. Such quaternary salts are broad spectrum bactericides, fungicides and algicides, highly effective against gram negative organisms even in hard water. They are also useful as intermediates for the synthesis of quaternary phosphonium clays.

19 Claims, No Drawings

SURFACE ACTIVE QUATERNARY HIGHER DIALKYL PHOSPHONIUM SALTS

FIELD OF THE INVENTION

This invention is related to surface active quaternary phosphonium salt biocides having two higher alkyl groups. One aspect of the invention relates to such salts, particularly to certain higher dialkyl lower dialkyl phosphonium chlorides as novel compositions having unexpected properties. Another aspect relates to the use of such salts as surfactants and biocides having unexpected effectiveness in hard water.

PRIOR ART

Although surface activity and the biological properties of the various types of quaternary higher alkyl ammonium salts were widely studied, the corresponding phosphonium salts received little attention in the past as shown by the monograph on "Cationic Surfactants" by E. Jungermann which was published by M. Dekker, Inc. in New York, N.Y. in 1970. Knowledge is particularly scarce about quaternary higher dialkyl phosphonium salts, especially the chlorides.

The primary disclosure on the latter compounds was made in U.S. Pat. No. 3,230,069 by W. H. Preston, Jr., which makes an all-inclusive statement on plant growth inhibition by tetraalkyl phosphonium halides having $C_1$ to $C_{16}$ substituents. This patent specifically discloses didodecyl and ditetradecyl dimethyl-phosphonium chlorides:

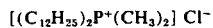

and

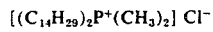

However, Preston does not specifically dislcose the preparation or properties of these compounds.

The only published preparation of a quaternary higher dialkyl phosphonium salt is by H. R. Hays in an article which appeared in the "Journal of Organic Chemistry" in volume 31, on page 3819 in 1966. Hays described the reaction of didodecyl phosphine with methyl iodide in methanol yielding didodecyl dimethyl phosphonium iodide.

The surface activity and biocidal properties of quaternary higher monoalkyl phsophonium halide salts, in general, were disclosed in U.S. Pat. No. 3,281,365 by K. Moedritzer. This patent also makes an all-inclusive disclosure of such compounds with the general formula,

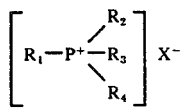

wherein $R_1$ is a $C_6$ to $C_{24}$ aliphatic group; $R_2$ to $R_4$ are $C_1$ to $C_{12}$ hydrocarbyl radicals and X is Cl, Br, I. However, Moedritzer does not specifically disclose any quaternary higher dialkyl phosphonium salt.

While work in the area of quaternary higher alkyl ammonium salts resulted in the commercial development of a large number of cationic surfactants and biocides no phosphonium salts were developed. In view of the increasing demands on the safety and effectiveness of such cationic compounds, a systematic study, partly disclosed in the present invention, but not claimed, was started to synthesize novel quaternary higher alkyl phosphonium salts and to study their properties and uses.

In the present invention, it was found that certain novel surface active quaternary higher dialkyl phosphonium salts are particularly effective broad spectrum biocides and surfactants. For example, in contrast to the previously disclosed quaternary didodecyl dimethyl phosphonium chloride, the closely related but novel didecyl dimethyl phsophonium chloride is an outstanding biocide. Unlike the higher monoalkyl compounds of Moedritzer, the present compounds are effective against gram negative bacteria and maintain their activity in hard water. Other novel compounds, such as the dioctadecyl deithyl phosphonium chlorides are particularly suitable intermediates for the preparation of tetraalkyl phosphonium clay gelling agents described in our copending U.S. Pat. application, Ser. No. 402,465 filed on Oct. 1, 1973, now U.S. Pat. No. 3,929,849.

SUMMARY OF THE INVENTION

Quaternarization of the appropriate secondary and/or tertiary aliphatic phosphines with primary alkyl chlorides at atmospheric pressure yields hydrochloride complexes of the corresponding higher dialkyl phosphonium chlorides. These complexes lose HCl in vacuo at elevated temperatures to yield the free phosphonium chloride salts. These salts have unexpected surfactant and biocide properties and as such, are surprisingly useful. They can be also be employed as intermediates for the synthesis of the corresponding phosphonium clays.

PRODUCT COMPOSITIONS

The quaternary phosphonium salts, preferably chlorides, of the present invention have two higher alkyl and two lower alkyl substituents. The preferred compounds can be represented by the general formula:

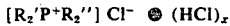

wherein R' is a $C_8$ to $C_{30}$ high and R" is a $C_1$ to $C_4$ low aliphatic hydrocarbyl radical selected from the group consisting of open chain alkyl, alkenyl and alkynyl radicals, x is 0 or 1. All the radicals are independently selected except that, in case the R' groups are dodecyl or tetradecyl and x is 0, the R" groups cannot both be methyl.

A more preferred group of compounds has the general formula:

wherein r is 8 to 30, preferably 9 to 18; s is 1 to 4, preferably 2 to 4, x is 0 or 1. The r and s values are independently selected, except that in case of s being one and r being 12 to 14, x cannot be 0. The symbol r is more preferably either 9 or 11 or 16 to 18. It is preferred that at least both of the higher alkyl radical substituents of the above phsophonium chlorides should be primary alkyl groups. It is furthermore preferred that the primary higher alkyl groups be straight chain moieties. It is most preferred that at least one of the lower alkyl groups be primary isobutyl.

Particularly preferred compounds have the general formula:

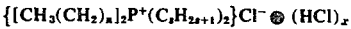

wherein $n$ is 15 to 17 and $s$ is 1 to 4, preferably 2 to 4,

wherein $m$ is 8 to 10, preferably 9, $s$ is 1 to 4, preferably 1.

Among the unsymmetrical phosphonium compounds particularly preferred are those of the formula:

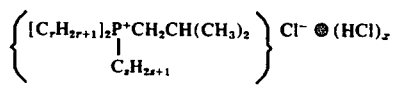

wherein the meaning of $r$ and $s$ is the same as before and the specifically preferred meaning of $s$ is 2.

Examples of phosphonium chlorides include those having the following specific quanternary phosphonium cation moieties: dioctyl dibutyl phosphonium, dihexatriacontyl dimethyl phosphonium, ditriacontyl dietyl phosphonium, dioctadecyl dipropyl phosphonium, docosyl dodecyl diisobutyl methyl phosphonium, dioctadecenyl dimethyl phosphonium, didocosyl dipropargyl phosphonium, octadecyl octadecenyl ethyl propargyl phosphonium, didodecyl diisopropyl phosphonium, dihexadecyl diisobutyl phosphonium, dioctadecyl dimethyk phosphonium, diundecyl diisobutyl phosphoium, doctyl diisobutyl phosphonium, dioctyl ethyl isobutyl phosphonium, didodecyl tertiary butyl methyl phosphonium, didecyl diisopropyl phosphonium, polysobutenyl dodecyl dimethyl phosphonium.

The phosphonium chloride compositions of the present invention have unexpected surfactant and biological properties. These properties are inherent in the structure of these compositions, namely, the bonding of two higher and two lower aliphatic hydrocarbyl groups to the tetracovalent phosphorus. Similar phosphonium chloride compositions having one higher alkyl and one lower alkyl group per phosphorus do not exhibit comparable properties.

In view of the prior work on quanternary higher monoalkyl phosphonium salts, it was completely unexpected that the present quanternary higher dialkyl phosphonium salts of a well defined type of structure, falling within the known broad, generic term tetraalkyl phosphonium chloride, would have unexpected and highly superior properties. In particular, it was found that the present compounds have unique combinations of unexpected properties: surfactancy, gelling ability, broad spectrum bactericidal-fungicidal-nematocidal action, high activity against gram negative bacteria, hard water resistance and low mammalian toxicity.

The two higher dialkyl dimethyl phosphonium chlorides, i.e. the didodecyl and ditetradecyl phosphonium compounds, previosly dislosed, do not possess the biological properties of the present compounds.

The hydrogen bonded hydrochloride complexes of the present quaternary higher dialkyl phosphonium chlorides are the primary products in their preparation. They are unexpectedly stable thermally, and exhibit the biocidal properties of the free salts. It these complexes are subjected to high temperatures at reduced pressures, they lose the hydrogen chloride. Such complexes of the formula:

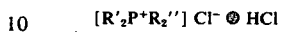
and

are generally novel and can also be used as clay reactants.

PROCESS OF PRODUCT PREPARATION

The quaternary phosophonium compounds of the present invention are prepared from the corresponding secondary or tertiary aliphatic phosphines via atmospheric quaternarization by primary alkyl chlorides. The novel phosphine intermediates of the present products and their quaternarization will be claimed separately. The general methods for the preparation of the present products are the following.

Secondary, higher or lower dialkyl phosphines can be quaternarized with the corresponding primary alkyl chlorides, e.g.

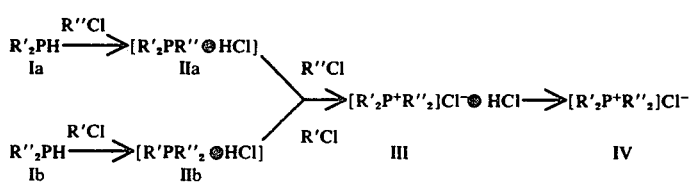

The first products of secondary phosphine (Ia and b) alkylation are the corresponding tertiary phosphine hydrochlorides (IIa and B). These are not accumulated in the reaction mixture, indicating their increased reactivity for further alkylation. The first isolable products of the reaction sequence are the quaternary phosphonium chloride hudrochloride complexes (III). These complexes are stable under the usual conditions at temperatures of about 80° to 200° C. However, when they are placed under vacuum at these elevated temperatures they are converted to the free quaternary salts, IV, on losing hydrogen chloride.

When starting with the higher dialkyl phosphine (Ia), the above alkylations can be surprisingly carried out at atmospheric or relatively low pressures, at up to 5 atmospheres, at temperatures above the boiling points of the lower alkyl chloride reactants. In such atmospheric alkylations, the lower alkyl chloride (R"Cl), preferably methyl chloride, is introduced at approximately the reaction rate into the alkylating vessel, containing the phosphine. Such alkylations are especially facile when methyl chloride is used.

The thermal stability of the novel phosphonium salts and their complexes is much higher than that of their ammonium analogs. Consequently, preferred high reaction temperatures in the range of 150° to 250° C can be employed, dependent on the reactants, without significant product decomposition. The high thermal stability usually allows one to operate without a solvent which otherwise would be needed to accelerate the reaction and/or to dissolve a product which is solid at lower temperatures. Of course, solvents may be used.

As solvents usually those are chosen which are known to accelerate $S_N^2$ reactions and are stable under the extreme reaction conditions. For example, dimethyl formamide is a preferred solvent.

The corresponding unsymmetrical trialkyl phosphines (Va and b) can also be used as starting materials for the production of the present quaternary higher dialkyl phosphinium chlorides:

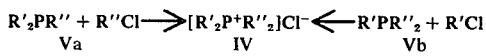
$$\underset{Va}{R'_2PR''} + R''Cl \longrightarrow \underset{IV}{[R'_2P^+R''_2]Cl^-} \longleftarrow \underset{Vb}{R'PR''_2 + R'Cl}$$

This method is particularly advantageous if the unsymmetrical phosphonium chlorides are desired wherein the two R' and/or two R'' groups are different.

The trialkyl phospines are more reactive towards the primary alkyl chloride reactants than the secondary phosphines. Trialkyl phosphine alkylations with methyl chloride can be carried out at temperatures as low as 80° C. In the case of the lower alkyl chloride reactants, the reactions again proceed at atmospheric or near atmospheric pressures up to 5 atmospheres at temperatures as high as 200° C. In general, the preferred reaction temperature ranges from 80 to 200° C. In general, it is preferred to introduce the smallest alkyl substituent of the product via the chloride reactant (R''Cl) of this scheme. Otherwise, the alkylation of tertiary phospines is similar to that of the secondary phosphines. Gaseous reactants are introduced preferably at about their rate of absorption. Solvents are again optional, the preferred solvent being dimethyl formamide.

SURFACTANT AND BIOCIDAL COMPOSITIONS

As previously noted, the quaternary higher dialkyl lower dialkyl phosphonium salts of this invention are useful as surfactants and biocides. The preferred compounds can be represented by the general formula:

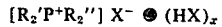
$$[R_2'P^+R_2''] \ X^- \bullet (HX)_x$$

wherein R' is a $C_8$ to $C_{30}$, preferably $C_9$ to $C_{18}$, high aliphatic radical and R'' is a $C_1$ to $C_4$ low aliphatic hydrocarbyl radical, both independently selected from the group consisting of open chain alkyl, alkenyl and alkinyl radicals, X is an anion selected from the group consisting of negatively charged inorganic and organic nonradical species. Such inorganic anions include halides such as chloride, bromide, fluoride; phosphates, such as polyphosphates; phosphite, sulfate tetrafluoroborate, nitrite and nitrate. Organic anions include carboxylates, having 1 to 30, preferably 1 to 18, carbon atoms, such as acetate, benzoate neotridecanoate, ethylenediamine tetraacetate; organic phosphate, phosphonate and phosphite anions such as $C_2$ to $C_6$ dialkyl dithiophosphate, phosphate, phosphite and phosphonate; $C_1$ to $C_{30}$ hydrocarbon sulfonate such as methanesulfanote, benzenesulfonate, tetrapropylenesulfonate; $C_1$ to $C_{24}$, preferably $C_1$ to $C_{12}$ alkyl sulfate such as methylsulfate, docosylsulfate, the symbol $x$ is 0 or 1, preferably 0.

Chloride anions are most preferred because of t the unexpected ease of preparation of the chloride salts and their surprisingly high effectiveness. Finally $x$ is 0 or 1, preferably 0.

A more preferred group of compounds has the general formula:

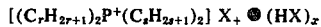
$$[(C_rH_{2r+1})_2P^+(C_sH_{2s+1})_2] \ X_+ \bullet (HX)_x$$

wherein $r$ is 8 to 30, preferably 9 to 18; $s$ is 1 to 4, preferably 2 to 4; and X, $x$ are the same as before. It is preferred that the higher alkyl substituents of the above phosphonium salt compounds should be primary alkyl groups. It is furthermore preferred that the primary higher alkyl groups be straight chain moieties. It is particularly preferred that at least one of the low alkyl groups be isobutyl.

The particularly preferred anions of the above surfactants and/or biocides are chloride, fluoride, sulfate; alkyl sulfates, carboxylates, phosphates, phosponates, phosphites. Specifically preferred are chlorides and fluorides. Most preferred are chlorides.

The anion of the above salts may be free or hydrogen bonded with a protic acid derived from the same or another anion.

The particularly preferred compounds to be used for producing clay derivatives have the general formula:

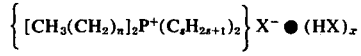
$$\left\{ [CH_3(CH_2)_n]_2P^+(C_sH_{2s+1})_2 \right\} X^- \bullet (HX)_x$$

wherein $n$ is 7 to 29, preferably 15 to 17 and $s$ is 1 to 4, preferably 2 to 4, and X, $x$ are the same as before.

Another particular subgroup of compounds specially useful as biocides is of the formula:

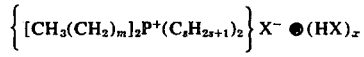
$$\left\{ [CH_3(CH_2)_m]_2P^+(C_sH_{2s+1})_2 \right\} X^- \bullet (HX)_x$$

wherein $m$ is 7 to 29, preferably 8 to 18, more preferably 9 to 10, $s$ is 1 to 4, preferably 1, 2, 4 and X, $x$ are the same as before.

Among the unsymmetrical compounds are particularly preferred, both as biocides and surfactants, those of the formula:

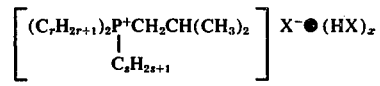
$$\left[ \begin{array}{c} (C_rH_{2r+1})_2P^+CH_2CH(CH_3)_2 \\ | \\ C_sH_{2s+1} \end{array} \right] X^- \bullet (HX)_x$$

wherein the meaning of $r$, $s$ and X, $x$ are the same as before for the preferred compounds.

As it will be shown by examples, the surfactant compositions of the present invention are surprisingly effective in reducing liquid to gas, particularly water to air, surface tension when employed in low concentrations ranging from 0.5 to 0.0001, preferably 0.1 to 0.001%. These compositions are particularly effective in reducing liquid to liquid, particularly water to organic liquid, specifically hydrocarbon, interfacial tension. In these latter applications, concentrations ranging from 0.5 to 0.00001, preferably 0.01 to 0.0001% may be used. Similarly, these surfactants may be used for reducing the interfacial tension among liquids and solids and as such may have a detergent action. In the various applications based on the surfactant properties of our phosphonium compounds the concentration depends on the effectiveness in the particular practical system. In contrast to laboratory systems consisting of pure known components, other components, such as impurities, different natural and synthetic surfactants, are likely to be present in commercial use. In general, the effective concentration of the present higher dialkyl phosphonium compounds is surprisingly lower than that of the related higher monoalkyl phosphonium compounds. The effectiveness of the present phosphonium surfactants is particularly surprising in reducing interfacial tension.

Typical surfactant applications, such as detergent, flotation, emulsification uses, are reviewed by E. Jungermann in a mongraph entitled "Cationic Surfactants", which was published by M. Dekker, Inc. in 1970 in New York, N.Y. This review shows that these applications are commercial for ammonium cationics but unknown for the present phosphonium compounds as noted on page 197 of the monograph.

The biocidal effect of the present quaternary higher dialkyl phosphonium salts is primarily exhibited against organisms selected from the group consisting of Protophyta, Thallophyta, viruses and invertebrates.

The biocidal, preferably microbiocidal, compositions of the present invention are unique, compared to the known quaternary phosphonium salts because of their activity against gram negative bacteria, particularly the Pseudomonancae family, Pseudomonas genus, *Pseudomonas aeruginosa* species. Furthermore, they are unique in their ability to maintain this bactericidal effectiveness in hard water. They are also surprising in having a broad microbiocidal spectrum, i.e. activity.

The microbiocidal activity of the present compositions is unexpectedly broad. It includes primitive plants, Protophyta; algae, molds and yeasts, Thallophyta. Among the primitive plants, unexpected activity is observed against bacterial organisms, Schyzomycetes class and bluegreen algae, Schyzophycae class. The bacterial organisms are defined in Bergey's "Manual of Determinative Bacteriology", published by the Williams and Wilkins Co., Seventh Edition, Baltimore, Md., 1957.

The present compounds are highly active against gram positive organisms such as *Streptococcus pyogenes*, important in sanitation; *Staphylococcus aureus* which is important, e.g., in the cosmetics field; *Bacillus mycoides*, significant in slime formation. High activity against gram negative organisms includes, for example, *Escherichia coli* and *Salmonella typhosa*, important in the sanitation field; *Aerobacter aerogenes*, often involved in slime formation; *Pseudomonas stutzeri*, frequently attacking cosmetics, and other *Pseudomonas* species, attacking crude and fuel oils. High activity is also observed against acid fast bacteria such as *Mycobacterium tuberculosis*.

The present compositions are unexpectedly effective against Thallophyta, namely the yeasts and yeast-like fungi and molds and mold-like fungi. These fungal organisms, when involved in attacking industrial products, are often designated as mildew. Among the medical monilias which are controlled by the present compositions, is the yeastlike *Candida albicans*, important in several human infections, e.g. thrush, vaginitis and fingernail infections. High activity is also observed against mold type fungi important in aspergillosis and dermatophytosis. For example, *Aspergillus fumigatus* important in pulmonary diseases, and *Trychophyton interdigitale*, important in foot infections, are controlled.

The various classes of fungi which can be controlled by the present compositions are listed on pages 163 to 166 in the "Handbook of Microbiology" by M. B. Jacobs and M. J. Gerstein, which was published by the Van Nostrand Reinhold Co. in New York, N.Y., 1960. The medically important fungi controlled by the present compositions are discussed in Chapter 32 of the "Textbook of Microbiology" by W. Burrows, which was published by the W. Saunders Co., in Philadelphia, Pa., 1959.

The antiviral activity of the present compounds is to be also included among their microbiocidal effects. As far as the broader biocidal effects are concerned, it is noted that the present compositions are active against invertebrates such as *Culex quinquefasciatus;* the larvae of mosquitoes, *Aedes aegypti;* worms and molluscs.

As far as the activity against molds and yeasts is concerned, it includes mildew causing fungi, such as *Penicillium glaucum*, *Penicillium luteum*, *Penicillium funiculosum*, *Aspergillus flavus*, *Aspergillus oryzae*, *Chaetomium globosum*, *Trichoderma viride* and *Pullularia pullulans*. Activity against these fungal organisms is important for industrial biocides, i.e. mildewcides. Other fungal organisms, important in agriculture and oil products, are also controlled by the present compositions.

The algae and protozoa, which are surprisingly controlled by the present products, include the *Eurocaryotic* algae such as the brown and red algae. Specific exemplary organisms are *Chlorella pyrenoidosa* and *Chlorella vulgaris*. The *Eurocaryotic* algae are reviewed on page 102 of the "Microbial World" by R. V. Stanier, M. Doudoroff and E. A. Adelberg, published by Prentice-Hall, Inc., Englewood Cliffs, N.J., 1963.

The exact degree of activity of the present microbiocides is, of course, dependent on their chemical structure, the microorganism involved, and on the other components of the environment, i.e. biosystem. For example, in aqueous media, the water hardness usually has an adverse effect on the effectiveness of the microbiocide. Cationic, anionic, and nonionic surfactants and proteins may also interfere with the activity. Other components of detergents may also have an effect.

The above considerations are discussed in detail in Chapter 14 on the "Germicidal Properties of Cationic Surfactants" of the earlier referred Jungermann monograph.

The effectiveness of the present compositions particularly depends on their chemical structure when used against organisms of the genus *Pseudomonas* such as *Pseudomonas aeruginosa*. For example, in the case of higher dialkyl dimethyl phosphonium chlorides, only compounds of di-$C_9$ to $C_{11}$-alkyl substitution are active against these organisms. In the case of the i-butyl substituted quaternary higher dialkyl phosphonium salts, a high level of effectiveness is exhibited by compounds regardless of the exact length of the higher alkyl groups.

The higher dialkyl phosphonium compounds in general exhibit decreased mammalian oral toxicities as the alkyl chain length increases. Nontoxic compounds of surprising microbiocidal effectiveness were obtained when the number carbon of the n-alkyl chains was 16 or higher per chain.

Microbiocidal activity of known quaternary salts is particularly unsatisfactory in hard water against certain gram negative bacteria such as *Escherichia coli*. The compounds of the present invention are surprisingly effective in such cases.

Obviously, the selection of a single, surface active microbiocide of the present invention or a combination of microbiocides and surfactants involving at least one of the present compounds depends on the exact nature of the application. This selection is greatly facilitated for persons trained in the art by the surprising generic and subgeneric properties of the present compositions and alows them to use more effective formulations, which are for example, useful as detergent antiseptics, disinfectants, by having the present compounds as constituents in effective amounts.

The present invention provides compositions of increased surfactancy and increased biocidal properties containing as a minor component, the quaternary higher dialkyl lower dialkyl salts of the present invention, in amounts sufficient to provide said surface active and biocidal properties in said compositions. According to the present invention, compositions are also provided which have either increased surfactancy or increased biocidal properties. Furthermore, compositions are provided which have increased biocidal properties against certain classes, geni and specii of organisms. Under biocidal properties, both the killing of organisms and the inhibition of their growth are included. More specific phosphonium salt components can be preferred as disclosed earlier.

The major components of liquid and/or solid systems, wherein the present biocides are used, are well known in the prior art. For example, the systems where fungicides are used are described in Volume I on Chapters 6 to 11 of a monograph "Fungicides" edited by D. C. Torgeson and published by Academic Press, Inc., New York, N.Y., 1967. Particularly, Chapter 6 discusses the various types of formulations: dusts, e.g. kaolinite, calcium carbonate; water dispersible powders, emulsions and solutions. Chapters 7 to 9 describe the various agricultural applications such as foliar, seed and soil treatments and post-harvest uses for preserving crops. Chapter 10 enumerates the main industrial preservative applications involving textiles, paper and pulp, rubber, plastics and paint, electrical and electronic equipment, petroleum products, leather, drugs and cosmetic preservatives. Finally, Chapter 11 is on wood preservatives. Similarly, various formulations are used in the bactericidal and algicidal field. However, in the bactericidal field, usually living organisms are protected from pathogenic bacteria. Consequently, in this field, biocides are mainly used to fight bacterial infections and to preserve drugs and cosmetics. The major medium of action for bactericides is therefore water and organic liquids, preferably solvents such as hydrocarbons, e.g. paraffins and alcohols, e.g. hexadecyl alcohol; esters, e.g. glycerides. In the case of algicides, of course, water medium is involved. Accordingly, the major component of the present biocidal compositions is selected from the group consisting of water, organic solvents, powders, elastomers, plastics, textiles, leather, cosmetics, drugs, petroleum products.

In some cases, the present higher dialkyl lower dialkyl phosphonium salts are used in minor amounts for the sole purpose of increasing surface activity. The major amount of the compositions is preferably selected from the group consisting of water and organic liquids. For the reduction of surface tension, the present compounds are preferably employed in water. Applications for the reductions of interfacial tension preferably involve water and hydrocarbon liquids.

In the same maner, a method of changing the surface and biocidal properties of compositions by applying thereto minor amounts of a quaternary phosphonium salt, having two higher alkyl and two lower alkyl substituents, in effective amounts, is provided. Such a method can be specially directed to reduce the surface tension of a composition. Another specific feature of the invention, is a method reducing the interfacial tension of normally immersible compositions. A further part is a method of inhibiting in their habitat, the growth of organisms as specified previously. Finally, a method of killing organisms previously described comprising applying to their habitat, minor amounts of said quaternary phosphonium salts in effective amounts is provided.

EXAMPLES

A. Syntheses (1 – 8)

The structures of the eight quaternary higher dialkyl phosphonium chlorides, whose synthesis will be illustrated with examples, are shown with their melting range and elemental composition in Table I. This listing of compounds in the Table is in the order of their increasing molecular weight. The description of their preparation in examples, however, is arranged according to the chemistry involved. In general, the conversions were complete and the yields were quantitative. Losses dependent on the solvents used, occurred on recrystallization.

a. Quaternarization of Secondary Phosphines (1 – 4)

In the first four examples, the quaternarization of higher di-n-alkyl phosphines with methyl chloride is illustrated. The first two of these examples also describe the primary quaternary phosphonium chloride - hydrogen chloride complexes of such reactions and their conversion to the corresponding free salts, which can be followed via the downfield chemical shift of the α-methyl doublet signals.

b. Quaternarization of Tertiary Phosphines (5–8)

The second group of four examples describes the quaternarization of trialkyl phosphines. The first three examples of this group show the quaternarization of higher di-n-alkyl lower monoalkyl phosphines with lower alkyl chlorides. The last example illustrates the other approach starting with a higher mono-n-alkyl lower dialkyl phosphine and a higher n-alkyl chloride.

TABLE I

Some Physical and Analytical Data of Quaternary Higher Dialkyl Phosphonium Chlorides

| Sequence No. | Structure of Phosphonium Cation | Melting Range, °C | Elemental Composition, % | | | | | | | |
|---|---|---|---|---|---|---|---|---|---|---|
| | | | Calculated | | | | Found | | | |
| | | | C | H | P | Cl | C | H | P | Cl |
| 1 | $(C_8H_{17})_2P^+(CH_3)_2$ | 128–134$^a$ | 66.95 | 12.49 | 9.59 | 10.97 | 68.54 | 12.45 | 9.61 | 10.83 |
| 2 | $(C_8H_{17})_2P^+(CH_3)C_2H_5$ | 104–108$^a$ | 67.73 | 12.56 | 9.19 | 10.52 | 67.33 | 12.22 | 9.07 | 10.22 |
| 3 | $(C_9H_{19})_2P^+(CH_3)_2$ | 165–168$^a$ | 68.44 | 12.64 | 8.82 | 10.10 | | | | 10.06 |
| 4 | $(C_{10}H_{21})_2P^+(CH_3)_2$ | 172–176$^a$ | 69.71 | 12.77 | 8.17 | 9.35 | 69.73 | 12.91 | 8.19 | 9.37 |
| 5 | $(C_{12}H_{25})_2P^+(CH_3)_2$ | 127–132$^b$ | 71.77 | 12.98 | 7.11 | 8.14 | 70.65 | 12.48 | 7.16 | 8.81 |
| 6 | $(C_{12}H_{25})_2P^+(C_2H_5)CH_2CH(CH_3)_2$ | 53–56$^a$ | 73.35 | 13.13 | 6.30 | 7.22 | 73.31 | 13.51 | 6.29 | 6.95 |
| 7 | $(C_{16}H_{33})_2P^+(C_2H_5)CH_2CH(CH_3)_2$ | 60–67$^b$ | 75.63 | 13.36 | 5.13 | 5.88 | 75.16 | 13.42 | 5.07 | 6.57 |

TABLE I-continued

Some Physical and Analytical Data of Quaternary Higher Dialkyl Phosphonium Chlorides

| Sequence No. | Structure of Phosphonium Cation | Melting Range, °C | Elemental Composition, % | | | | | | | |
|---|---|---|---|---|---|---|---|---|---|---|
| | | | Calculated | | | | Found | | | |
| | | | C | H | P | Cl | C | H | P | Cl |
| 8 | $(C_{18}H_{37})_2P^+(C_2H_5)_2$ | 80-83[b] | 76.08 | 13.41 | 4.90 | 5.61 | 76.65 | 13.72 | 5.09 | 5.56 |

[a]Crude product after removal of volatiles.
[b]Recrystallized.

EXAMPLE 1 - Didodecyl Dimethyl Phosphonium Chloride

Into a Pyrex glass cylindrical reaction vessel, equipped with a Teflon needle valve and a magnetic stirrer, were placed 18.05 g (0.05m) of didodecyl phosphine reactant and 4.1 g (0.1m) of acetonitrile solvent. The vessel was then cooled by dry ice, and evacuated. Thereafter, 6.4 g (0.126m) of methyl chloride reactant was condensed into the vessel. The vessel was then closed and heated with stirring to 80° C in 35 minutes and kept there for 5 hours.

The didodecyl phosphine was not miscible with the acetonitrile. However, on heating the mixture at 80° C, a homogeneous liquid mixture resulted in 10 minutes. After 5 hours at 80°, the nuclear magnetic resonance spectrum of a sample indicated an essentially complete quaternarization, by exhibiting the expected intensity of the protons on the carbons next to the phosphonium moiety, particularly a methyl doublet at 2.0 ppm.

The crude reaction mixture was then evacuated to 100 mm at ambient temperature to remove the methyl chloride. A subsequent phosphorus and chlorine analysis and the nmr chemical shift of the doublet signal of the α-methyl groups of the residual product (at 2.05 ppm from TMS with coupling constant, $J_{P-C} = 14$ cps) indicated that the resulting quaternary phosphonium chloride was in the form of a hydrochloride complex.

The residual product was heated to 100° C at 0.2 mm for 90 minutes to remove all the acetonitrile. The solvent-free residue was dissolved in an equal amount of refluxing toluene. The position of the methyl doublet at 2.38 ppm in the nmr spectrum of the resulting solution indicated that a significant portion of the salt was still in the complex form. On cooling to −20° C, crystallization of most of the product from toluene occurred. On filtration by suction in a nitrogen box, 12g (73%) of the free salt, exhibiting an nmr methyl doublet at 2.53 ppm with a $J_{P-C}$ of 14.5 ppm in benzene was obtained.

EXAMPLE 2 - Dinonyl Dimethyl Phosphonium Chloride

Into a cyclindrical vessel, equipped with a sintered glass gas inductor, in and out bubblers, and a magnetic stirrer, is placed 2.83 g (0.1m) of dinonyl phosphine under nitrogen. The stirred phosphine is then heated to 120° C and kept at that temperature while methyl chloride was introduced into it at a rate sightly greater than its absorption. After 6 hours at 180° C, a weight gain of 8.5 g was observed. An additional seven hours resulted in 0.5 g more weight gain, which was determined after purging any dissolved methyl chloride with nitrogen. A complete quaternarization of the dinonyl phosphine by methyl chloride to form the hydrochloride complex of the desired quaternary phosphonium chloride should have resulted in a total of 10.1 g weight gain.

The crude complex reaction product solidified to a gel-like substance at room temperature. Most of it was melted, poured into a distilling flask and heated with nitrogen capillary bubbling at 200° in high vacuo to remove all volatiles. By the end of the heating, the vacuum improved from 0.5 to 0.005 mm. No dinonyl phosphine was recovered in the receiver, indicating its complete quaternarization. The less than theoretical weight of the crude complex was due to a partial loss of HCl during the reaction. The subsequent heating in vacuo resulted in a complete HCl loss and a quantitative yield of the free salt as a residual product. This sequence of reactions is supported by the nmr spectra of samples. The partially decomposed complex in deuterobenzene exhibited an α-methyl doublet at a chemical shift value of 2.33 ppm ($J_{P-C}$ 14 cps). In the free salt, this signal shifted downfield, as in the previous example, to 2.63 ppm ($J_{P-C}$ 15 cps).

EXAMPLE 3 - Didecyl Dimethyl Phosphonium Chloride

In the manner described in the previous example, 31.4g (0.1 m) of didecyl phosphine was reacted with methyl chloride at 180° C for 8 hours. A complete quaternarization and a partial dissociation of the primary complex product were observed again. On subsequent heating at 200° under 0.15 mm for 3 hours, the expected free quaternary phosphonium chloride was obtained in a quantitative yield. This product solidifies to form a colorless, waxy solid at room temperature. Its nmr spectrum exhibits a characteristic doublet for the α-methyl protons at 2.62 ppm ($J_{P-C}$ 15 cps).

EXAMPLE 4 - Dioctyl Dimethyl Phosphonium Chloride

As described in the previous two examples, 25.8 g (0.1 m) of dioctyl phosphine was reacted with methyl chloride at 180° C for 6 hours to form a mixture of the desired quaternary phosphonium chloride and its hydrochloride complex. Subsequent heating, at 200° under 0.4 mm for 3 hours provided the free salt in a 97% yield as a colorless waxy solid at room temperature. The characteristic α-methyl doublet of this product in deuterobenzene appears at 2.58 ppm ($J_{P-C}$ 15 cps).

EXAMPLE 5 - Dioctyl Ethyl Methyl Phosphonium Chloride

Into 14.4 g (0.5m) of dioctyl ethyl phosphine, placed in the bubbler reactor described in Example 2, methyl chloride was introduced at 130° C for 4 hours. The degree of weight gain observed corresponded to a quantitative formation of the desired product; a colorless, waxy solid at room temperature. In the nmr spectrum of this product, the α-methyl doublet appears at 1.93 ppm ($J_{P-C}$ 14 cps).

The product is highly soluble in toluene even at low temperatures. It is precipitated from toluene by n-heptane.

EXAMPLE 6 - Didodecyl Isobutyl Ethyl Phosphonium Chloride

Into the bubbler reactor of Example 2, 34.2 g (0.1 m) of didodecyl primary isobutyl phosphine was placed under nitrogen. Then ethyl chloride was introduced in the usual manner at 200° for 15 hours to form the desired quaternary chloride in a quantitative yield. The product is a colorless solid at room temperature. It is highly soluble in toluene.

EXAMPLE 7 - Dihexadecyl Isobutyl Ethyl Phosphonium Chloride

In the manner described in the previous example, 27 g (0.05 m) of dihexadecyl primary isobutyl phosphone was quantitatively reacted with ethyl chloride at 200° C in 12 hours. The amount of ethyl chloride absorbed indicated that the reaction was already essentially complete in 6 hours. Most of the quaternary chloride product, 30g, a colorless solid at room temperature, was recrystallized from 100 ml hot n-heptane. Crystallization started at room temperature. The mixture was nevertheless cooled to −25° and filtered cold under nitrogen with suction. After drying in vacuo, 26.5 g (88%) of recrystallized product was obtained.

EXAMPLE 8 - Dioctadecyl Diethyl Phosphonium Chloride

In the first experiment, a magnetically stirred mixture of 8.5 g (0.25m) octadecyl diethyl phosphine and 7.2g (0.25m) octadecyl chloride was heated in a cylindrical reaction vessel under nitrogen at 190° for 24 hours. The absence of the chloromethyl nmr triplet signal, in a sample of the mixture after 3 hours, indicated that most of the conversion occurred during the first few hours. The crude product was a colorless solid at room temperature and exhibited the expected nmr spectrum. It was recrystallized from 50 ml hot methyl ethyl ketone. After filtration and rinsing at room temperature, the recrystallized product was dried at 0.2 mm at ambient temperature. The yield of the dry purified product was 75%.

In the second experiment, 342 g (1m) of the octadecyl diethyl phosphine reactant was added during the course of 80 minutes to 289g (1m) of the stirred nitrogenated octadecyl chloride at 190°. Heating of the reaction mixture was continued for 3 hours after the completion of the addition. Thereafter, the mixture was allowed to cool to 140' and at that temperature methyl chloride was introduced into it to quaternarize any traces of unreacted phosphine. The resulting crude product was then recrystallized from 1200 ml of methyl ethyl ketone to yield 587g (93%) of the desired purified quaternary phosphonium chloride.

B. Surfactant Tests (9)

To obtain standard data for estimating the surface activity of quaternary higher dialkyl phosphonium salts, the surface tensions of their water solutions and the interfacial tensions of their equilibriated solutions in water and a paraffinic hydrocarbon were determined as described by ASTM D-971-50.

EXAMPLE 9 - Effectiveness in Reducing Surface and Interfacial Tension

Didodecyl dimethyl phosphonium chloride and, for comparison, octadecyl trimethyl phosphonium chloride were tested as described above, according to ASTM D-971. The surface tension towards air measurement used distilled water at 25°, which gives a base value of 72 dynes per cm. For interfacial tension measurements a water-paraffin (Nujol) system was used. Without any added surfactant, this has an interfacial tension of 52 dynes per cm. The interfacial tension measurements of the phosphonium chloride solutions were made after equal volumes of the two immiscible instead and the given amount of salt were slowly stirred for 30 minutes to arrive at equilibrium concentrations of the salt. The data are shown in Table II.

The tension data show that the quaternary higher dialkyl compound is a much more effective surfactant than the corresponding monoalkyl derivative. It is effective in reducing both surface tension and interfacial tension when present at a concentration of 0.001%. In contrast, the monoalkyl compound is relatively ineffective even at a hundred times greater concentration. In comparison to all known surfactants, the ability of the quaternary higher dialkyl phosphonium salts is particularly outstanding in reducing interfacial tension.

C. Biocidal Tests

In the primary biocidal testing of the quaternary higher dialkyl phosphonium salts, broth dilution was used as the primary method to determine the minimum salt concentrations necessary for complete inhibition of bacterial, fungal and algal growth. Typically, 2 ml per tube of trypticase soy broth was used as nutrient medium. Usually 10 mg of the phosphonium chloride was dissolved in 5 ml ethanol and this was then diluted to 10 ml with water to give an aqueous ethanol stock solution of 2000 ppm concentration.

TABLE II

Surface Activity of a Quaternary Higher Dialkyl Phosphonium Chloride Versus the Corresponding Higher Monoalkyl Derivative

| Chemical Structure of the Cation of the Quaternary Chloride | Tension Data, Dynes/cm, at 25° (at Various Salt Concentrations, %) | | | | | |
|---|---|---|---|---|---|---|
| | Surface Tension of Water | | | | | |
| | (0.100) | (0.010) | (0.0075) | (0.005) | (0.0025) | (0.001) |
| $(C_{12}H_{25})_2P^+(CH_3)_2$ | 29 | 31 | 31 | 32 | 33 | 33 |
| $C_{18}H_{37}P^+(CH_3)_3$ | 41 | 42 | — | — | — | — |
| | Interfacial Tension of Water-Nujol | | | | | |
| | (0.100) | (0.010) | (0.0075) | (0.005) | (0.0025) | (0.001) |
| $(C_{12}H_{25})_2P^+(CH_3)_2$ | 2 | 3 | 3 | 3 | 3 | 3 |
| $C_{18}H_{37}P^+(CH_3)_3$ | 10 | 12 | — | — | — | — |

The inoculum of the microorganism was one drop of a thousand fold diluted 24 hour culture which usually contained 1000 bacteria or 10,000 fungal or algal cells. To the inoculated broth media, different amounts of the experimental chemicals were administered. The media were than observed for visible growth after a period dependent on the type of the microorganism used. Bacterial growth or inhibition was observed after one or two days. Growths of fungi and algae were checked after 7 or 14 days. When observing a series of dilutions of the experimental chemical, minimum growth inhibitory, i.e., microbiostatic, concentrations (MIC) were determined.

EXAMPLE 10 - Activity Against Growth of Representative Bacteria, Fungi and Algae A number of quaternary phosphoinium chlorides characterized in Table I were broth dilution tested against an important gram negative bacterial organism, *Pseudomonas aeruginosa;* a common gram positive bacterium, *Staphylococcus aureus*, and a widespread fungus, *Aspergillus niger*, and a common algal organism, *Chlorella vulgaris*. The test results are shown in Table III.

The results indicate striking differences in the activity of the various phosphonium chlorides against the most difficult to control organism, *Pseudomonas aeruginosa*. Against this species of the Pseudomonas genus, the known didodecyl dimethyl phosphonium chloride (Seq. No. 4) shows no significant activity. As it is indicated by their much lower minimum inhibitory concentrations, the activity of the novel quaternary higher dialkyl phosphonium salts is much higher. Particularly outstanding in their activity are didecyl dimethyl phosphonium chloride (Seq. No. 3), didodecyl and dihexadecyl isobutyl ethyl phosphonium chlorides (Seq. Nos. 6 and 7).

rium, *Staphylococcus aureus*. However, these organisms show much less structure specificity in their response to the various quaternary phosphonium chlorides.

EXAMPLE 11 - Microbiocidal Spectrum of Didecyl Dimethyl Phosphonium Chloride

To test the breadth of the microbiocidal spectrum of didecyl dimethyl phosphonium chloride, minimum inhibitory concentrations (MIC's) were determined against several additional organisms in broth dilution tests with the following results:

Against gram negative bacterial organisms, important in sanitation, i.e. *Escherichia coli* and *Salmonella typhosa*, the MIC's were 0.5 and 8 ppm, respectively. Against the yeast-like fungus, *Candida albicans*, important in thrush, vaginitis and other human infections, the MIC found was 0.25 ppm.

EXAMPLE 12 - Bactericidal Effectiveness In Hard Water

To determine the effectiveness of a quaternary higher dialkyl phosphonium salt, i.e. didecyl dimethyl phosphonium chloride as a bactericide, the AOAC Germicidal and Santitizer Test was used. The results are shown by Table IV. The high kill by the higher dialkyl compound of the bacteria in the soft, distilled water and a simikill in the hard water shows a bactericidal effect which is surprisingly insensitive the water.

TABLE IV

Bactericidal Activity in Distilled and Hard Water of a Quaternary Higher Dialkyl Phosphonium Chloride Versus a Higher Monalkyl Derivative both at a Concentration of 25 ppm

| Chemical Structure of the Cation of the Quaternary Chloride | Bacterial Micro-organism | Reduction of Live Organisms | |
|---|---|---|---|
| | | In Distilled Water | of 200 ppm Hardness |
| $(C_{10}H_{21})_2P^+(CH_3)_2$ | Staph. aureus | 99.999 | 99.999 |
| | E. coli | 99.999 | 99.900 |
| $C_{20}H_{41}P^+(CH_3)_3$ | Staph. aureus | 99.999 | 92 |
| | E. coli | 99.999 | 61 |

In contrast the activity of the highly effective higher monoalkyl compound is drastically reduced when employed in hard water.

TABLE III

Microbiocidal Activity of Quaternary Higher Dialkyl Phosphonium Chlorides Against Representative Bacteria, Fungi and Algae

| | | | Minimum Inhibitory Concentration, ppm (After Days) | | | |
|---|---|---|---|---|---|---|
| Sequence Number | (Example Number) | Structure of Phosphonium Cation | Pseudo-monas aeruginosa | Staphylo-coccus aureus | Aspergillus niger | Chlorella vulgaris |
| 1 | (4) | $(C_8H_{17})_2P^+(CH_3)_2$ | 250(1) | 0.5(2) | 7.5(14) | 4(14) |
| 2 | (5) | $(C_8H_{17})_2P^+(CH_3)C_2H_5$ | 250(2) | | | |
| 3 | (3) | $(C_{10}H_{21})_2P^+(CH_3)_2$ | 16(1) | 0.5(2) | 0.25(14) | 0.125(14) |
| 4 | (1) | $(C_{12}H_{25})_2P^+(CH_3)_2$ | 2500(1) | 1.0(1) | 75(7) | 8(7) |
| 5 | (6) | $(C_{12}H_{25})_2P^+(C_2H_5)CH_2CH(CH_3)_2$ | 16(1) | 0.5(1) | 1.0(14) | 0.5(14) |
| 6 | (7) | $(C_{16}H_{33})_2P^+(C_2H_5)CH_2CH(CH_3)_2$ | 16(1) | 0.5(1) | 0.5(14) | 0.5(14) |
| 7 | (8) | $(C_{18}H_{37})_2P^+(C_2H_5)_2$ | 500(2) | 15(2) | 15(14) | 7.5(14) |

The biocidal activity differences are also clearly shown on the fungus, *Aspergillus niger*. Against this organism, the minimum inhibitory concentration of the novel didecyl dimethyl phosphonium chloride (Seq. No. 3) was three hundred times smaller than that of the known didodecyl dimethyl phosphonium chloride (Seq. No. 4).

The same trend of activities are observed against the alga, *Chlorella vulgaris* and the gram positive bacte- EXAMPLE 13 - Toxicity Towards Mammals The acute oral toxicity of didecyl dimethyl phosphonium chloride and dioctadecyl diethyl phosphonium chloride was determined using Swiss albino mice. The median lethal toxicities found were 350 and 2840 mg salt per body kg mice, respectively. This means a medium level of oral toxicity for the didecyl compound and an essential lack of oral toxicity for the dioctadecyl compound. Due to its lack of toxicity the latter compound, although not highly active microbiocidally, appears surprisingly attractive for some fungicidal applications.

What is claimed is:

1. Quaternary phosphonium chlorides of the formula:

$$[R_2'P^+R_2''] \ Cl^- \bullet (HCl)_x$$

wherein $R'$ is a $C_8$ to $C_{30}$ high open chain alkyl, and $R''$ is a $C_1$ to $C_4$ low aliphatic hydrocarbyl group selected from the group consisting of open chain alkyl, alkenyl and alkinyl groups, $x$ is 0 or 1; all the groups being independently selected, except, that in case the $R'$ groups are dodecyl or tetradecyl and $x$ is 0, the $R''$ groups cannot both be methyl.

2. Quaternary higher dialkyl lower dialkyl phosphonium chlorides having the formula:

$$[(C_rH_{2r+1})_2P^+(C_sH_{2s+1})_2] \ Cl^- \bullet (HCl)_x$$

wherein $r$ is 8 to 30, $s$ is 1 to 4, $x$ is 0 or 1, except that if $r$ is 12 to 14 and $s$ is 1, $x$ cannot be 0.

3. A composition of increased surface activity containing as a minor component a surface active quaternary higher dialkyl lower dialkyl phosphonium salt of the formula:

$$[R_2'P^+R_2''] \ X^- \bullet (HX)_x$$

wherein $R'$ is a $C_8$ to $C_{30}$ high alkyl group, $R''$ is a $C_1$ to $C_4$ low aliphatic hydrocarbyl independently selected from the group consisting of open chain alkyl, alkenyl and alkinyl, X is an anion selected from the group consisting of halides, phosphates, phosphites, sulfates, tetrafluoroborate, nitrites, nitrates, $C_1-C_{30}$ carboxylates, organic phosphates, phosphonates, phosphites, $C_1$ to $C_{30}$ hydrocarbon sulfonates and $C_1-C_{24}$ alkyl sulfates, and $x$ is 0 or 1; in effective surfactant amounts the major component being selected from the group of water and organic liquids.

4. Compounds according to claim 2, wherein $r$ is 9 to 11, $s$ is 1 to 4 and $x$ is 0 or 1.

5. Compounds according to claim 2, wherein $r$ is 16 to 18, $s$ is 1 to 4 and $x$ is 0 or 1.

6. Quaternary higher di-n-alkyl lower dialkyl phosphonium chlorides having the formula:

$$[(CH_3(CH_2)_n]_2P^+(C_sH_{2s+1})_2] \ Cl^- \bullet (HCl)_x$$

wherein $n$ is 15 to 17 and $s$ is 1 to 4, $x$ is 0 or 1.

7. Compounds according to claim 6, wherein $s$ is 2 to 4.

8. Quaternary higher di-n-alkyl lower di-alkyl phosphonium chlorides having the formula:

$$\{[CH_3(CH_2)_m]_2P^+(C_sH_{2s+1})_2\}Cl^- \bullet (HCl)_x$$

wherein $m$ is 8 to 10, $s$ is 1 to 4.

9. Compounds according to claim 8 wherein $s$ is 1.

10. Quaternary higher dialkyl lower monoalkyl isobutyl phosphonium chlorides having the formula:

$$[(C_rH_{2r+1})_2\underset{C_sH_{2s+1}}{P^+}CH_2CH(CH_3)_2] \ Cl^- \bullet (HCl)_x$$

wherein $r$ is 8 to 30, $s$ is 1 to 4 and $x$ is 0 or 1.

11. Compounds according to claim 10 wherein $s$ is 2.

12. Didecyl dimethyl phosphonium chloride.

13. Didodecyl isobutyl ethyl phosphonium chloride.

14. Dioctadecyl diethyl phosphonium cloride.

15. A composition according to claim 3 wherein said phosphonium salt component has X anions selected from the group consisting of halides, phosphtaes, sulfates, sulfonates, tetrafluoroborate, nitrate, and nitrite.

16. Compounds according to claim 1 wherein $x$ is 0.

17. Compounds according to claim 1 wherein $x$ is 1.

18. Dinonyl dimethyl phosphonium chloride.

19. Dihexadecyl isobutyl ethyl phosphonium chloride.

* * * * *